United States Patent [19]
Eggers et al.

[11] Patent Number: 5,308,311
[45] Date of Patent: May 3, 1994

[54] ELECTRICALLY HEATED SURGICAL BLADE AND METHODS OF MAKING

[75] Inventors: Philip E. Eggers, Dublin, Ohio; Robert F. Shaw, 1750 Taylor St., San Francisco, Calif. 94108

[73] Assignee: Robert F. Shaw, San Francisco, Calif.

[21] Appl. No.: 877,698

[22] Filed: May 1, 1992

[51] Int. Cl.⁵ ............................................. A61B 17/38
[52] U.S. Cl. ...................................... 606/28; 606/31; 606/45; 606/29
[58] Field of Search ........................ 606/27, 28, 29, 30, 606/31, 32, 34, 37, 38, 39, 40, 41, 42, 45, 49

[56] References Cited

U.S. PATENT DOCUMENTS

| | | | |
|---|---|---|---|
| Re. 31,723 | 11/1984 | Shaw | 606/31 |
| 3,768,482 | 10/1973 | Shaw | 128/303.1 |
| 3,826,263 | 7/1974 | Cage et al. | 128/303.1 |
| 4,161,950 | 7/1979 | Doss et al. | 128/303.14 |
| 4,231,371 | 11/1980 | Lipp | 606/31 |
| 4,314,559 | 2/1982 | Allen | 606/45 |
| 4,364,390 | 12/1982 | Shaw | 606/29 |
| 4,481,057 | 11/1984 | Beard | 156/216 |
| 4,485,810 | 12/1984 | Beard | 128/303.1 |
| 4,754,754 | 7/1988 | Garito et al. | 128/303.14 |
| 4,770,067 | 9/1988 | Liu et al. | 76/104 R |
| 4,785,807 | 11/1988 | Blanch | 128/303.14 |
| 4,802,476 | 2/1989 | Noerenberg et al. | 128/303.14 |
| 4,848,337 | 7/1989 | Shaw et al. | 606/28 |
| 4,850,353 | 7/1989 | Stasz et al. | 128/303.14 |
| 4,862,890 | 9/1989 | Stasz et al. | 128/303.14 |
| 4,958,539 | 9/1990 | Stasz et al. | 76/104.1 |

Primary Examiner—Peter A. Aschenbrenner
Attorney, Agent, or Firm—Nicola A. Pisano

[57] ABSTRACT

A hemostatic surgical blade and methods of manufacturing such blades are provided, wherein the blade comprises a laminate region having a hardenable center layer and highly thermally conductive outer layers, joined to a second region of a low thermal conductivity material. A heating element is secured to the laminate region and in thermal communication therewith to thermally reform the collagen of tissue as it is incised. The heat generated by the heating element is conducted to the cutting edge of the blade to maintain the cutting edge temperature within 20° C. to 70° C. of a user-selected operating temperature. The second region reduces the conduction of heat to the handle of the instrument. The heating element comprises a thermally conductive dielectric layer attached to an outer surface of the laminate region, resistive conductive elements deposited on the dielectric, a second dielectric layer covering the resistive conductor elements, and an abherent coating disposed thereon to reduce coagulum buildup on the blade.

29 Claims, 4 Drawing Sheets

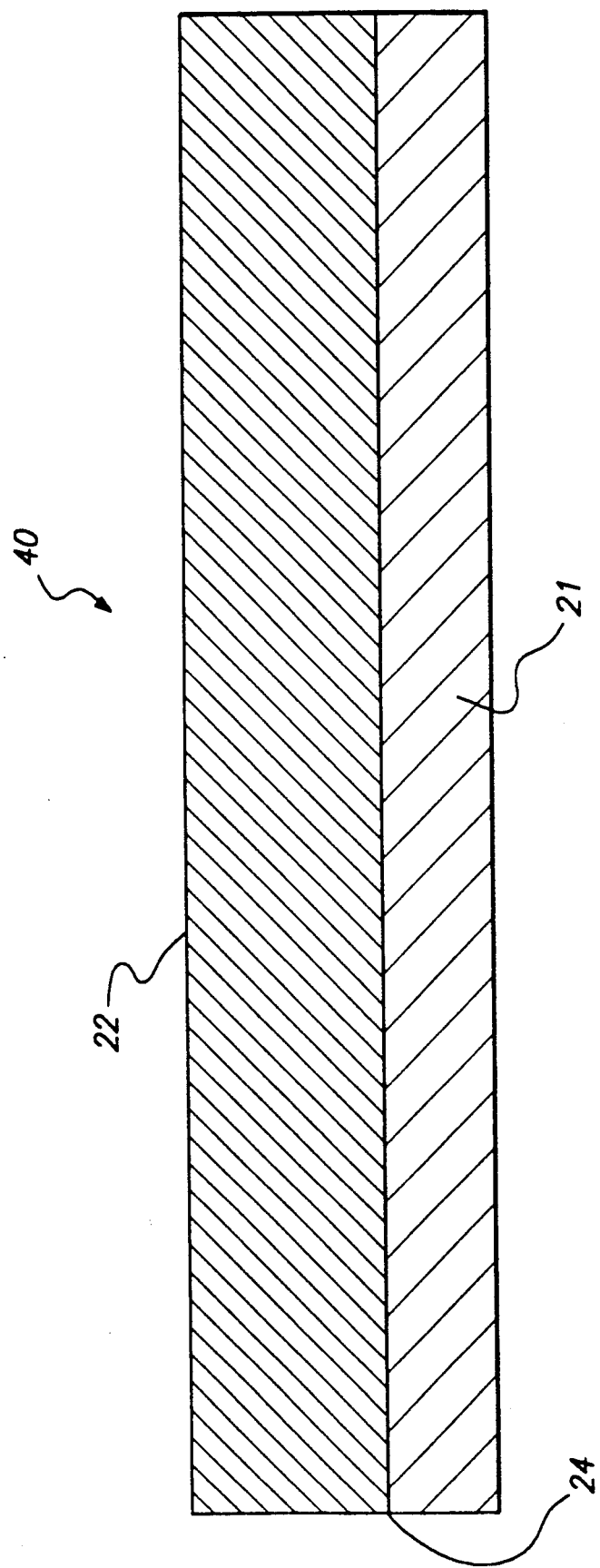

ELECTRICALLY HEATED SURGICAL BLADE AND METHODS OF MAKING

This invention relates to heated surgical instruments, particularly to improved blade structures for thermally autoregulated hemostatic instruments, such as scalpers.

BACKGROUND OF THE INVENTION

The control of bleeding during surgery accounts for a major portion of the time involved in an operation. In particular, bleeding that occurs when tissue is incised obscures the surgeon's vision, delays the operation, and reduces the precision of cutting.

One technique for minimizing the bleeding of tissue as it is being severed is known as hemostatic surgery. This technique uses a heated instrument to contact bleeding tissue. The heat is transferred from the instrument to the incised (or torn) tissue to reform thermally collagen, thereby producing a thin collagenous film that seals over the severed blood vessels and capillaries, thereby reducing bleeding. Because heat is applied locally to tissue that contacts the heated region of the instrument, there is little tissue necrosis or damage that, if present, would retard healing.

One such hemostatic instrument is known as a hemostatic surgical scalpel. This scalpel has a sharp cutting edge similar to that of a conventional steel scalpel blade, and a heating element proximate to the cutting edge to heat the blade. During cutting, the scalpel blade is heated and the heat is transferred to the tissue being cut.

One commercial device using this technique is the Shaw Hemostatic Scalpel, manufactured and sold by the Hemostatic Surgery Corporation, San Francisco, Calif., and described in U.S. Pat. Nos. 3,768,482, 30,190, 4,481,057, and 4,485,810. This device uses a multi-segmented resistive heating element whereby the current flowing through each segment is individually controlled to maintain each segment, and hence the blade, within a narrow range of user-selected temperatures.

A drawback of previously known hemostatic heated scalpel blades has been the inability to deliver an adequate quantity of heat in close proximity to the cutting edge, to maintain a sharp durable cutting edge, and to be usable for sustained surgery under a wide variety of surgical cutting applications. Sufficient thermal delivery is critical to seal promptly the blood vessels and capillaries being severed. The quantity of heat that must be delivered increases with the rate at which the scalpel is being moved through the tissue and the degree of vascularization of the tissue. These conditions have limited the cutting rate and depth that the previously known devices can be used to hemostatically cut tissue.

Good surgical blades are commonly made of hard materials such as steels and martensitic stain less steels, but these materials generally have low thermal conductivity. High thermal conductivity materials are desirable for delivering the necessary heat, but typically do not maintain a sharp and durable cutting edge. Contact of the high thermal conductivity blades with the corrosive biological fluids and operation at elevated temperatures combine to dull the cutting edges of such blades prematurely. Moreover, they also conduct large amounts of heat to the handle of the blade, making it uncomfortable for the surgeon to hold the instrument during surgery.

Attempts to use other blade materials have been made without any apparent success, e.g., ceramic blades as described in Shaw U.S. Pat. No. 3,768,482, Johnson U.S. Pat. No. 4,219,025, Lipp U.S. Pat. No. 4,231,371, and high thermal conductivity materials treated to have hardened cutting edges as described in U.S. Pat. No. 4,770,067. These devices similarly lack the combination of desirable thermal transfer properties and a durable sharp cutting edge.

Other types of hemostatic scalpel devices having non-segmented heating elements for heating the sharp scalpel blades are described in U.S. Pat. Nos. 4,207,896, 4,091,813 and 4,185,632.

Accordingly, there is a continuing need to provide a sharp, durable scalpel blade capable of delivering sufficient thermal energy to the tissue to cause hemostasis under a wide variety of operating conditions.

SUMMARY OF THE INVENTION

In view of the foregoing, it is an object of the present invention to provide an improved surgical blade for hemostatically cutting tissue, and methods of making such blades.

It is another object of this invention to provide a sharp, durable, scalpel blade having improved thermal delivery capabilities over a broad range of conditions encountered in surgical procedures.

It is another object of this invention to provide a sharp, durable, scalpel blade using corrosion resistant martensitic steel and methods of manufacturing the same for use in hemostatic surgical scalpels.

It is another object of this invention to provide a material for an electrically resistively heated film coating, and methods of applying the same, for use in heating a surgical instrument.

It is another object of this invention to provide a thermally autoregulated heated scalpel blade having a cutting region that is maintained at a nearly uniform temperature over the full range of surgical cutting conditions.

It is another object of this invention to provide a hemostatic scalpel blade that permits the sustained operation without restrictions imposed by the thermal delivery capabilities of the blade components.

It is yet another object of this invention to provide an electrically heated surgical blade that reduces conduction of heat from the heated region of the surgical blade to the blade support.

It is another object of the present invention to provide an electrically heated surgical blade having electrical leads characterized by a low electrical resistance, to reduce ohmic heating of the blade support by resistive losses in the electrical leads.

It is another object of this invention to provide a method of manufacturing a surgical blade to reduce thermal conduction from the heating element and tissue cutting regions of the blade to the handle supporting the blade.

This invention provides a surgical blade for contacting and heating tissue at elevated temperatures to reduce bleeding from incised tissue, comprising a first region of a material having a high thermal conductivity joined to a second region of a material having a low thermal conductivity. The blade includes a heating element for heating the first region to a temperature in the range of about 100° C. to about 500° C. This heating element is in thermal contact with, but electrically isolated from, the first region.

One embodiment of the present invention comprises a surgical blade for hemostatically cutting tissue, the surgical blade inserted into a handle having an electrical terminal, the blade comprising:

(a) a first region of a laminate material having a sharp cutting edge and lateral sides, the laminate comprising a core of high strength hardenable material and a pair of outer layers of a material having a high thermal conductivity, each one of the pair of outer layers being disposed on opposite sides of the core and in thermal communication therewith;

(b) a second region of a low thermal conductivity material, the second region being joined to the first region and having a portion adapted to engage the handle;

(c) a heating element for heating the first region to a temperature in the range of from about 100° C. to about 500° C., the heating element secured to the first region in thermal communication therewith and electrically isolated therefrom; and (d) an electrical lead for connecting the heating element to the electrical terminal of the handle.

The heating element may be located on one or both of the lateral sides of the first region, on the cutting edge of the first region, or on any combination of those surfaces.

In one embodiment of the apparatus, the heating element further comprises a first thin layer of dielectric material having high thermal conductivity disposed on the first region and a first conductor material disposed on the first dielectric material, the first conductor material having a first resistivity and a resistance that vary as a function of temperature. The electrical lead comprises a second thin layer of dielectric material disposed on the second region and a second resistive conductor material having a second resistivity equal to or less than the first resistivity, the second conductor material being disposed on the second thin layer of dielectric and in electrical contact with the first conductor material.

The heating element may comprise a plurality of segments, each of which is electrically connected to a plurality of electrical leads, so that the heating element segments are individually temperature controlled. A third dielectric material is preferably disposed on the heating elements and electrical leads to cover all but a portion of the electrical leads that connect to the electrical terminal of the instrument handle. In addition, a layer of an abherent material may be disposed on those portions of the blade that are likely to contact tissue during use. Also, a thin film of oxidation resistant material may be deposited on the cutting edge.

The surgical blade of the present invention has improved corrosion resistance, durability, strength, hardness and thermal transfer properties relative to previously known surgical blades. In the preferred embodiment, the blade comprises a laminate having a core comprising a martensitic steel, and outer layers, joined on opposite sides of the core, composed of a high thermal conductivity metal. The martensitic steel core provides a hardenable center layer that can be conventionally heat-treated to provide the composite laminate with a hardness of 57 Rockwell C or better. The martensitic steel layer can be configured to provide a sharp cutting edge, while the high thermal conductivity outer layers conduct heat from the heating element to the cutting edge.

Another aspect of the present invention is directed to an improved material for use as a film resistive heating element in a hemostatic surgical instrument, wherein the heating element is capable of withstanding elevated temperatures and nonuniform thermal loading. A preferred embodiment of the material is directed to a high-expansion dielectric material comprising metal-filled glass having a specific sheet resistance in the range of from about 10 to about 50 mΩ/mm at 20° C., a thermal expansion coefficient not less than about 12 microinches/inch/°C., and a resistance temperature coefficient of at least 0.0005 Ω/°C. and preferably greater than 0.002 Ω/°C. over the temperature range of about 20° to about 500° C.. Preferred glass materials include oxides of silicon, iron, sodium, potassium, calcium, chromium, aluminum, lithium, lead, zinc or combinations thereof. Preferred metal materials include finely divided silver, gold, aluminum, platinum, and tungsten.

The present invention includes methods of manufacturing an electrically heated surgical blade, comprising the sequence of steps of:

(a) providing a core of a high strength hardenable material having lateral faces and a pair of outer layers of a high thermal conductivity material;

(b) joining each one of the pair of outer layers to a lateral face of the core to form a laminate having a first thickness;

(c) providing a strip of a low thermal conductivity material;

(d) joining the laminate to the strip along a longitudinal joint to form a sheet;

(e) providing the sheet with a smooth surface at the longitudinal joint;

(f) plating the sheet with a metallic material selected from among the group consisting of chromium, nickel, platinum, or silver;

(g) heat treating the sheet by passing it under tension through a reducing atmosphere at an elevated temperature, and then cooling the sheet to obtain a high hardness level in the core of the first region; and (h) perforating the sheet to define at least one blade blank having a first region formed of the laminate and a second region formed of the strip.

The method further comprises forming each blank into a surgical blade by securing a heating element to the first region and sharpening the blade blank to provide a sharp cutting edge on the first region. This sharpening step may be performed either before or after the heating element is applied. The method therefore comprises the additional steps of:

(i) coating one side of the plated blank with a first layer of a high expansion dielectric material having a thermal expansion coefficient in the range of the thermal expansion coefficient of the pair of outer layers of the first region and the material of the second region;

(j) depositing a thin layer of a first resistive conductor material in a first pattern on the first layer of dielectric material;

(k) depositing a thin layer of a second resistive conductor material in a second pattern on the first dielectric layer superimposed over the second region, the second pattern overlapping the first pattern of first dielectric material so that the first and second resistive conductors are in electrical contact;

(l) depositing a second layer of dielectric material over the first and second patterns of resistive conductive material except for a portion of the second pattern that is left exposed to accommodate completing an electrical contact between the resistive conductor materials and the electrical terminal of the handle; and (m) sharpening the blade to form a sharpened blade having a cutting edge.

In addition, the methods of the present invention comprise further steps relating to the heat treatment and deposition of the various layers, including an abherent coating, on the blade surfaces.

BRIEF DESCRIPTION OF THE DRAWINGS

The above and other objects and advantages of the inventions will be apparent upon consideration of the following detailed description, taken in conjunction with the accompanying drawings, in which like reference characters refer to like parts throughout, and in which:

FIG. 4 is a side view of a sheet of surgical blade material manufactured in accordance with the methods of the present invention.

DETAILED DESCRIPTION OF THE INVENTION

Figure 1:
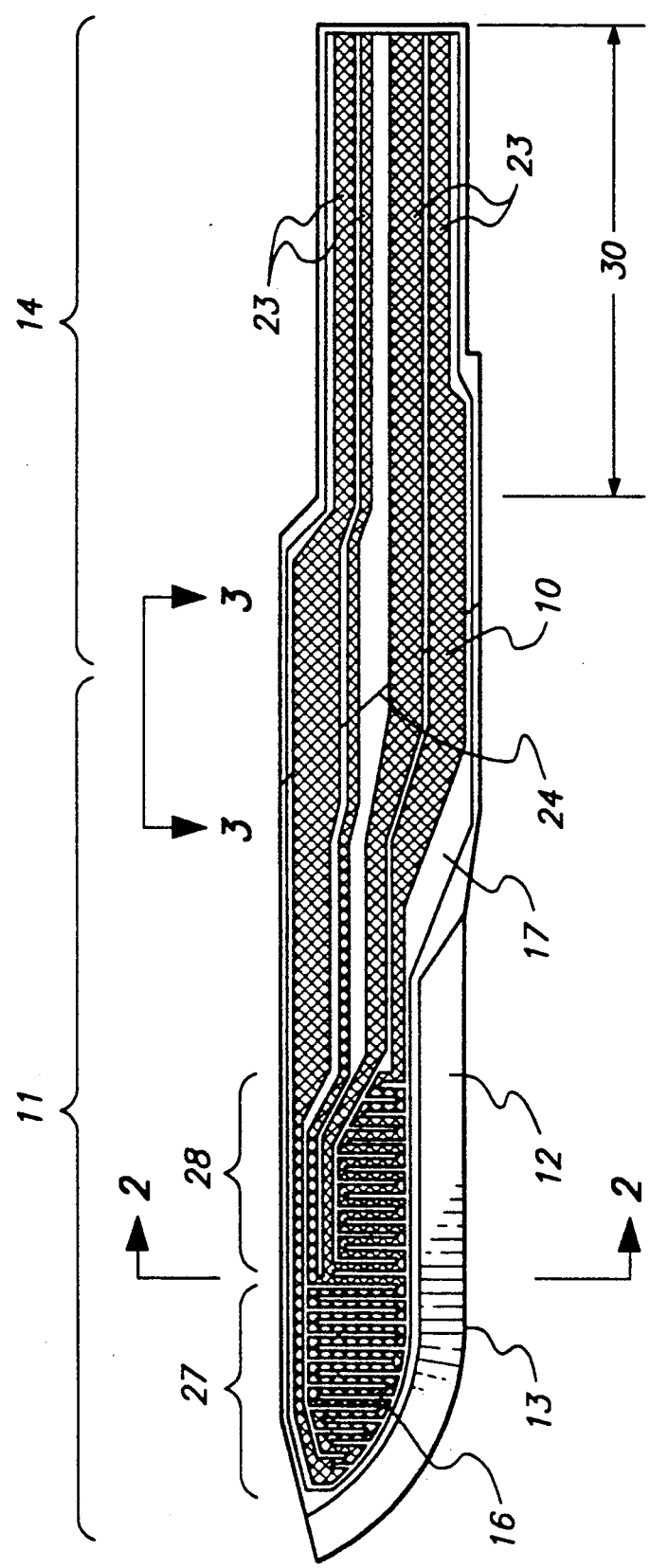
FIG. 1 is a side view of a surgical blade constructed in accordance with the present invention.
Figure 2:
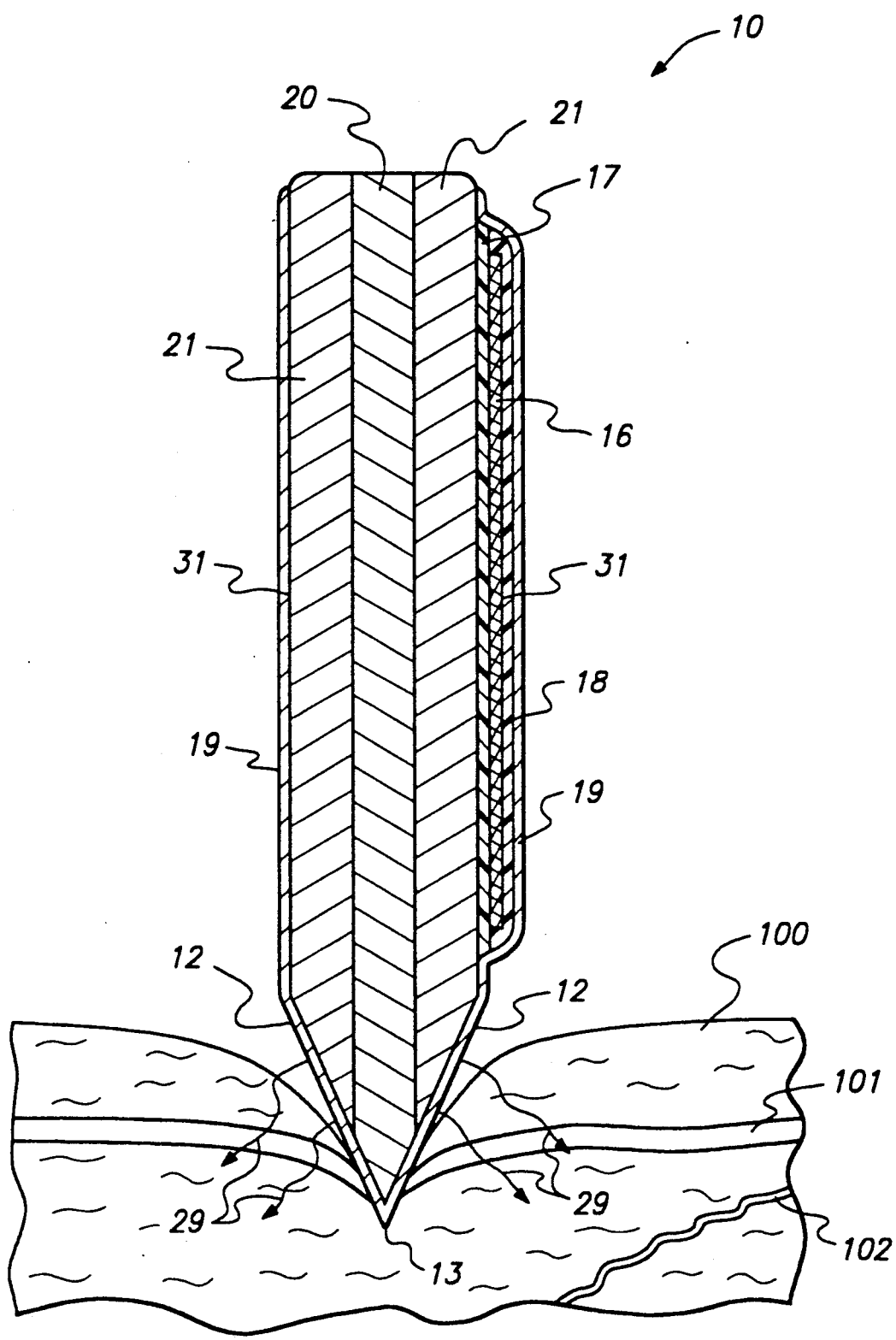
FIG. 2 is a cross-sectional view taken along line 2—2 of FIG. 1, showing the surgical blade contacting tissue.

Referring to FIGS. 1 and 2, surgical blade 10 constructed in accordance with the present invention is described. Surgical blade 10 is intended for use with a handle for supporting the blade, and is connected via a cable to a power source, as is conventional for electrically-powered resistively heated scalpel blades. The power source may be for example, one such as that described in copending and commonly assigned U.S. patent application Ser. No. 07/877,699, filed May 1, 1992 and includes panel switches for selecting the desired operating temperature of the device at, for example, a temperature range in the range from about 100° C. to about 500° C..

Blade 10 has a cutting region 11 near its distal end comprising faceted faces 12 that meet at sharp cutting edge 13 for incising tissue. Proximal portion 14 of blade 10 supports cutting region 11 and reduces the conduction of heat from cutting region 11 to the handle. Proximal portion 14 is dimensioned to fit securely within the handle (not shown) of the surgical instrument, for example, a scalpel handle.

Heating element 16 is disposed on cutting region 11 for heating that region and cutting edge 13 of blade 10. Heating means 16 comprises a trace or pathway of an electrically conductive material and is connected to an electrical lead that extends across proximal portion 14. That electrical lead is connected to an electrical terminal in the instrument handle, which is in turn connected to the power source via a cable.

An electrically insulating layer 17 is disposed on cutting region 11 and proximal portion 14 to electrically insulate heating element 16 from blade 10. A layer 18 of electrically insulating material is applied over heating element 16 to prevent the heating element from short circuiting through the patient's tissue. A coating 19 of abherent material may optionally be applied over that portion of blade 10 that contacts tissue, to reduce coagulum buildup on the blade during use.

In FIG. 2, cutting region 11 of blade 10 is shown in contact with, and severing, tissue 100, including blood vessels 101 and capillaries 102. To achieve the desired reforming of collagen into a film that seals blood vessels 101 and capillaries 102 while blade 10 is moving through tissue 100, blade 10 must be capable of conducting heat from heating element 16 to cutting edge 13 and faceted faces 12. In accordance with the present invention, the laminate structure of cutting region 11, described hereinafter, and electrically insulating layer 17 have high thermal conductivity to accomplish this task. Use of abherent coating 19 having high thermal conductivity further enhances the ability to transfer sufficient heat.

An advantage of the structure of the present invention is the ability to maintain the temperature of the heater element 16, blade 10, and faceted faces 12 of cutting edge 13 at substantially uniform levels, preferably within about 20° C. to about 70° C. of the user-selected operating temperature, and independent of the heat flux being transferred into tissue 100 during thermal loading. The user-selected temperature of operation is the steady state temperature of the device in still air, that is, in the absence of thermal loading. The heat flux during use depends upon the length of blade 10 in thermal contact with tissue 100, the rate at which the blade is moved through the tissue, and the user-selected operating temperature. A surgical blade constructed in accordance with the present invention has the ability to transfer large amounts of heat to the tissue, with little conduction of heat to the instrument handle.

As shown in FIG. 2, in a preferred embodiment, cutting region 11 comprises a laminate having a central core 20 and two outer layers 21. Central core 20 is a material having a high hardness and high mechanical strength, preferably a martensitic stainless steel, for example, AISI Type 440 C, or 420 C, or Hitachi Metal's product having the trade name h, GIN-4. The hardness level and edge sharpness of such alloys or other materials attained by heat treating central core 20 must be capable of withstanding subsequent processing conditions used in the manufacturing operation. For example, the hardness level must not deteriorate substantially when the core is exposed to high temperature processing conditions associated with joining outer layers 21, in depositing dielectric layer 18 on the blade, or when exposed to corrosive physiological fluids during operation at temperatures up to 500° C., as described hereinafter.

Outer layers 21 comprise a high thermal conductivity material to facilitate the transfer of heat generated by heating element 16 to cutting edge 13 of blade 10, more specifically, to the vicinity of the apex 11 of the cutting edge faceted faces 12. Outer layers 21 may be constructed of, for example, copper or more preferably an alumina dispersion strengthened copper containing from 0.1 to about 0.6 percent, by weight, of fine alumina particles. Outer layers 21 may be affixed to the lateral faces of core 20 using conventional metal fastening techniques, for example, roll-bonding or brazing, to form a multi-layer laminate. The pair of outer layers 21 are preferably constructed of the same material.

Outer layers 21 should have a thickness sufficient to maintain faceted faces 12 of cutting edge 13 in the distal portion of cutting region 11 at temperatures within from about 20° to about 70° C. of the user-selected operating temperature, for blade temperatures in the range of 100° C. to over 500° C. Central core 20 may be selected so that the majority of thermal energy transferred from heating element 16 to the patient's tissue is through faceted faces 12 of outer layers 21 rather than through the apex of cutting edge 13.

Cutting region 11 of blade 10 is sharpened to have a cutting edge 13 and faceted faces 12 along the periphery of the laminate structure used to contact and sever tissue, similar to conventional surgical blades. Faceted faces 12 each include a lower portion formed from central core 20 and an upper portion formed from outer layers 21. The apex of cutting edge 13 is preferably at or near the mid-thickness of center core 20, but other configurations could be used, depending upon the intended application of the surgical blade. The final sharpening, honing, buffing or stropping of faceted faces 12 results in cutting edge 13 which has the hardness and durability properties of central core 20 and heat transfer characteristics dominated by the thermal conductivity of outer layers 21.

Surgical blade proximal portion 14 comprises a material 22 having a low thermal conductivity, such as stainless steel AISI Type 304 or 304L. Region 14 supports cutting region 11 and has electrical leads 23 extending across it. Electrical leads 23 connect heating element 16 to the power source via connections to electrical terminals in the instrument handle and a cable. Proximal portion 14 reduces the thermal conduction of heat from heated region 11 of blade 10 to the handle, so that the handle does not become uncomfortably hot for the surgeon to manipulate. Materials having a thermal conductivity of 0.2 cal/sec/cm/°C. or less are suitable for use in proximal portion 14, and may be, for example, selected from the family of austenitic stainless steels.

Figure 3:
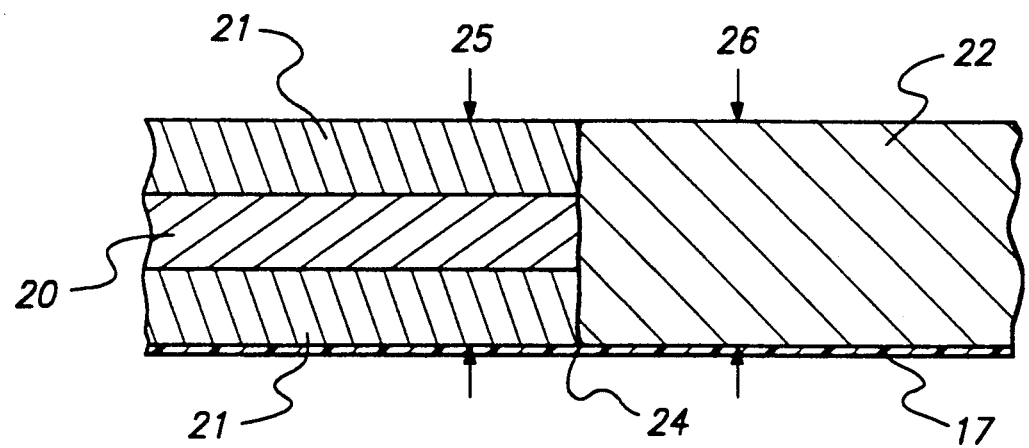
FIG. 3 is a cross-sectional view taken along line 3—3 of FIG. 1.

Cutting region 11 and proximal portion 14 are metallurgically joined as illustrated by bond line 24 in FIGS. 2 and 3. By the use of appropriate manufacturing techniques, such as welding, brazing or electron beam welding, a substantially smooth transition can be obtained between the multi-layer laminate of cutting region 11 and material 22 of proximal portion 14. This smooth transition is desirable to ensure that bond line 24 does not interfere with the further processing required to form a finished surgical blade.

The multi-layer laminate of cutting region 11 is formed by rolling core 20 and outer layers 21 together under pressure at elevated temperatures, i.e., hot rolled, to achieve a thickness 25. This process provides a bond of high mechanical (tensile) strength between the core and outer layers and provides an interface having high thermal conductance. Blade proximal portion 14 is then rolled from a low thermal conductivity metal to a thickness 26 that is close to or the same as thickness 25. Cutting region 11 and proximal portion 14 are then joined by any of the above-described metal fastening methods. Alternatively, proximal portion 14 may be thicker than cutting region 11, or may have a contoured surface that is about the same thickness at the interface and a different thickness away from the interface, while providing a smooth surface for dielectric layer 17 across the interface.

Heating element 16 heats to cutting region 11 to maintain cutting edge 13 at the selected operating temperature, and particularly, to compensate for heat loss due to radiation, convection, conduction, and thermal loads imposed on the blade during use in contacting and severing tissue. Heating element 16 provides thermal energy at a rate sufficient to effect reshaping of collagen into a film which seals over incised blood vessels during the brief time that cutting edge 13 is in contact with the tissue.

In a preferred embodiment, heating element 16 comprises a resistive conductive trace or pathway disposed on cutting region 11 in a serpentine path adjacent to cutting edge faceted faces 12. Electrical leads 23 extend from heating element 16 to proximal portion 14 of blade 10. Heating element 16 may be located on one or both of the lateral surfaces of blade 10 adjacent to cutting edge 13, depending upon the intended application of the surgical blade.

To electrically insulate heating element 16 from outer layer 21, a thin layer of high thermal conductance, dielectric material 17 is first deposited on the lateral surface of blade 10 adjacent to the cutting edge facets before the heating element is attached. To facilitate good adhesion between layer 17 and outer layer 21 of cutting region 11, and the material of proximal portion 14, the blade surfaces may first be coated with an oxidation resistant material, e.g., chromium. To provide for efficient heat transfer from heating element 16 to outer layer 21, layer 17 may comprise a thick-film printed, high-expansion glass, having a thermal expansion coefficient approximately matching the expansion coefficient of outer layer 21. Dielectric material 17 may be, for example, a glass material such as oxides of silicon, iron, sodium, potassium, calcium, chromium, aluminum, lithium, lead, zinc or combinations thereof, or diamond or a diamond-like form of carbon.

As shown in FIG. 1, heating element 16 preferably comprises two segments 27 and 28. Segment 27 heats the tip of the cutting region, while segment 28 heats the heel portion of the cutting region. Segments 27 and 28 are arranged in a pattern designed to create a uniform temperature in cutting region 11, despite the non-uniform construction of that region. Heating element 16 also includes a plurality of electrical leads 23 deposited in a second pattern that connects each of segments 27 and 28 to electrical terminals provided in the instrument handle. Electrical leads 23 permit the heating element segments to be separately controlled to maintain a uniform temperature in the blade, even for different thermal loading in the tip and heel regions. More or fewer heating element segments can be used as appropriate for the size and surgical application of the device.

The geometry of heating element 16 and electrical leads 23, that is, the cross sectional area and current path that define the resistance of the conductive elements, are selected to reduce joulean heating in proximal portions of electrical leads 23, so that energy is efficiently delivered to segments 27 and 28. Accordingly, heating element 16 and electrical leads 23 may be constructed of the same material, but applied in different dimensions. The heat generated by the controlled current flow in segments 27 and 28 is conducted to those regions of cutting edge 13 in good thermal communication with tissue, as illustrated by the heat flux lines 29 shown in FIG. 2.

Heating element 16 and electrical leads 23 may comprise, for example, a metal-filled glass-based conducting material having an expansion coefficient of not less than 12 microinches/inch/°C. and a temperature coefficient of resistance of at least 0.0005 per °C. in the temperature range from about 20° to about 400° C.. For example, fine silver particles less than about 0.001 inches in diameter dispersed in a glass material such as oxides of silicon, iron, sodium, potassium, calcium, chromium, aluminum, lithium, lead, zinc or combinations thereof, and similar materials, are suitable. Alternatively, heating element 16 and electrical leads 23 may comprise a polymer-based conducting material having a temperature coefficient of resistance of at least 0.0005 per °C. at temperatures in the range from about 20° C. to about 500° C., for example, silver-filled polymide thick film pastes available from Electro-Science Laboratories, Inc., King of Prussia, Pa.

The end portions of electrical leads 23 are exposed on proximal portion 14 of blade 10 and are adapted to contact corresponding spring contact electrical terminals, as described heretofore, mounted in the instrument handle. Blade 10 is preferably configured to extend length 30 into the handle, for example, about 0.2 to about 1.0 inch (5 mm to about 25 mm). The length of proximal portion 14 that extends beyond the instrument handle may be, for example, about 0.5 inch (12.7 mm) or greater, and serves to thermally isolate the heated (distal) end of blade 10 from the handle to prevent the handle from becoming uncomfortably hot during use. The blade and handle interconnection is designed so that blades 10 may be easily replaced when worn, and so that different blade configurations may be used with the handle during the same or different surgical procedures.

Heating element 16 also may comprise a material having either a positive or negative temperature coefficient of resistance, so that the resistance of the heating element varies as a function of temperature. If the heating element has a temperature coefficient of resistance of at least $500 \times 10^{-6}$ per °C., and preferably greater than $2,000 \times 10^{-6}$ per °C., the power source may be configured to sense a change in the heating element temperature by detecting a change in the heating element resistance. The power source can therefore adjust to the heat dissipation rates from the surgical blade during use, while maintaining the blade at a substantially constant temperature.

In an alternative embodiment (not shown), heating element 16 may be directly disposed on faceted faces 12 of cutting edge 13, for example, as described in Cage et al. U.S. Pat. No. 4,198,957.

A second layer of dielectric material 18 is disposed over heating element 16 and electrical leads 23 to electrically isolate those components from the patient's tissue. This second layer 18 comprises the same material as that described heretofore with respect to layer 17.

Abherent coating 19 may be disposed on all portions of blade 10 that contact tissue during surgery. Abherent materials have "non-sticking" properties that reduce the sticking or adherence of tissue, blood, coagulated blood and other biological fluids or residues to the blade during use, so called coagulum buildup. Advantageously, the use of an abherent coating reduces the added thermal impedance associated with coagulum buildup, which can reduce the hemostatic effect of the instrument. Abherent materials such as fluorinated polymers, fluorine containing inorganic compounds or silicone are suitable for use.

Abherent layer 19 should be deposited in a layer that is sufficiently thin, for example, less than 10 microns, to ensure good heat transfer from cutting region 11 of blade 10 to the tissue, whether from outer layers 21, faceted faces 12, or both, to achieve the desired sealing and cessation of blood flow. In addition, the abherent material should retain its non-stick properties at temperatures in the range from about 100° C. to about 350° C..

To provide for good adhesion between abherent layer 19 and its underlying substrate, portions of the blade may be coated with an optional metallic or nonmetallic coating 31 using conventional plating, thin film deposition, or vapor deposition techniques. In particular, coating 31 may improve adhesion between abherent coating 19 and exposed metallic surfaces of outer layers 21 not covered by electrically insulating layer 18, which surface might otherwise oxidize and permit coating 19 to slough off. Coating 31 of a thickness of about 3,000 to 5,000 Angstroms have been determined to provide satisfactory performance.

The methods and apparatus of the present invention are further described in connection with the following illustrative examples, with reference to FIG. 4.

EXAMPLE I

A surgical blade 10, for example a scalpel blade, may be constructed in accordance with a preferred embodiment of the present invention as follows. Multi-layer laminate strip 40 is formed by roll bonding two outer layers 21 of low-oxygen, alumina dispersion strengthened copper, SCM Corporation product designation AL-15 to AL-60 (preferably low-oxygen grade AL-25) to both lateral surfaces of central core 20 comprising stainless steel AISI Type 440 C or equivalent. The finished rolled thicknesses of copper outer layers 21 are equal on both sides of the stainless steel core 20 and range between 0.0007 and 0.030 inches (0.018 to 0.762 Mm); core 20 has a thickness of from 0.003 to about 0.015 inches (0.076 to 0.38 mm). The laminate has a width from the cutting edge to the top of the scalpel, ranging from 0.70 to about 1.40 inches, depending upon the blade size being manufactured.

A solid layer 22 of low thermal conductivity stainless steel (AISI Type 304 or 304L) is rolled to form a strip having about the same thickness as the multi-layer laminate. This strip has a width ranging from about 1.0 to about 3.0 inches.

The laminate and solid sections are then electron-beam welded together in vacuum to obtain a composite sheet 40 having a longitudinal joint or bond line 24. The composite sheet is then rerolled and/or ground using a grinding wheel to achieve a surface in the region of the weld zone that is sufficiently smooth to allow the deposition of dielectric layer 17.

Sheet 40 is then plated with a chromium or nickel layer about 100 to about 200 microinches thick. Alternatively, this plating step may be conducted subsequent to the heat treatment process.

Composite sheet 40 is then heat treated by mechanically passing the sheet through a conventional furnace. A reducing atmosphere, such as nitrogen, is provided within the furnace to prevent oxidation of the sheet surfaces. The heat treatment time and temperature are specified by the vendor of the material used for core 20, and differ depending upon the exact material. The duration of exposure and the temperature profile obtained in the sheet are selected to achieve a high hardness level in the stainless steel AISI Type 440 C at the core of the laminate portion of the sheet. Preferably, a hardness level of 57 to about 63 (Rockwell C scale) is achieved.

The heating step is immediately followed by passing the sheet between cooling platens, which quench the material to the final hardness and prevent warping of the sheet. The combined effects of the heat treatment provide the desired flatness of the sheet, which is important for application of the dielectric and heating elements and electrical leads by thick-film printing techniques, as well as for blade sharpening.

The plated heated-treated composite sheet is then perforated by an electro-discharge machining (EDM) or blanking operation to define blanks corresponding to the desired finished blade shape. The EDM or blade blanking operation is performed so that cutting region 11 of the blade is formed from the laminate of core 20 and outer layers 21, while proximal portion 14 is formed from the low thermal conductivity material 22.

When it desired to perforate the heat-treated composite sheet with an EDM process, it may be desirable to first cut the composite sheet 40 into lengths suitable for processing with the EDM equipment prior to performing the heat treatment step, for example 18-24 inches long. In this case, the strips may be heat treated using a vacuum furnace, and then quenched in a nitrogen atmosphere. Alternatively, if it is desired to perform the blade blanking step prior to the heat treatment step, the blade blanks may be retained in position in the blanked sheet via ligaments extending along the upper and lower region of the sheet.

The resulting plated blanks are then coated on one side with high-expansion glass dielectric that matches the thermal expansion coefficient of one or both outer layers 21 and proximal portion 14. To provide efficient heat transfer, it is desirable that layer 17 comprise a thick-film printed high expansion glass having a thermal expansion coefficient of approximately 12 to 18 microinches/inch/°C. The thick film printing step is followed by firing the coated blades in air to about 460° C. for about five minutes.

Next, heating element material 16 is thick film printed in a first pattern on dielectric 17 in region 11 of the blade blank. The heater material is preferably a metal filled glass containing silver to achieve a relatively high specific sheet resistance, e.g., 10 to 50 mΩ per square mm at 20° C., such as is available from Electro-Science Laboratories, Inc.

Electrical leads 23 are then formed of a silver filled glass material having a relatively low specific sheet resistance. e.g., 5 mΩ per square Mm at 20° C., such as those available from Electro-Science Laboratories, Inc. Electrical leads 23 are thick-film printed in a second pattern on dielectric 17 in proximal portion 14, and overlap the heating element film in cutting region 11 for a length of about 0.010 to about 0.020 inches to provide an electrical interconnection therebetween.

Optionally, overcoat dielectric material 18 may be printed over the entire printed heater element conductor film and most of the printed electrical lead film to electrically insulate the heater from the patient's body fluids and tissues. The proximal ends of the electrical lead film traces are left exposed to accommodate connection with the electrical terminals within the instrument handle. Alternatively, abherent coating 19 may serve to electrically insulate the blade from the tissue.

The resultant blank is sharpened conventionally using a multiple stage sharpening process that ends with a final honing or stropping operation. Thereafter, thin-film coating 31 of oxidation resistant metallic or non-metallic material, e.g., platinum, may be deposited on cutting edge faceted faces 12 exposed during sharpening, to a thickness of about 1,000 Angstroms. This is followed by application of a non-stick, abherent coating, e.g., Vydex 1000, which can be applied by dip coating followed by air drying at 120° C. for ten to thirty minutes and oven curing at 350° C. for ten to twenty minutes. Vydex 1000 is the tradename of a fluorotelemer material manufactured by Du Pont. Following the application of the non-stick coating, each finished blade is placed in an appropriate container and sterilized for use.

EXAMPLE II

An alternative process for manufacturing blades in accordance with the present invention follows the same sequence of steps for manufacturing blades as described in Example I, through forming the individual blade blanks. In this alternative process, the plated blade blank is then sharpened and coating 31 of oxidation resistant metallic or non-metallic material is applied to cutting edge faceted faces 12 exposed by the sharpening step. The remaining steps of the process are then performed in the same sequence as for the process described in Example I.

Laboratory tests have shown that blades constructed in accordance with above methods preferred embodiment, and having the same shape and size as a conventional No. 20 scalpel blade, dissipate in excess of 210 watts while operating at 300° C., when the side of the blade opposite the heating element is in contact with a moist sponge. In surgical studies involving animals, surgical blades constructed according to the present invention have been used to incise and simultaneously cause hemostasis of blood vessels as large as about 1.5 mm while operating at set point temperatures in excess of 200° C..

Scalpel blades manufactured in accordance with Examples I and II were tested and found to provide sufficient heat transfer and durability in retaining edge sharpness, kinesthetics similar to steel scalpels, and improved thermal isolation of the heated portion from the handle for sustained use at elevated temperatures. In particular, during use under widely varying thermal loading, faceted faces 12 were maintained within from about 20° C. to 70° C. of the user-selected operating temperature.

The present invention includes methods of manufacturing an electrically heated surgical blade, comprising the sequence of steps of:

(a) providing a core of a high strength hardenable material having lateral faces and a pair of outer layers of a high thermal conductivity material;

(b) joining each one of the pair of outer layers to a lateral face of the core to form a laminate having a first thickness;

(c) providing a strip of a low thermal conductivity material;

(d) joining the laminate to the strip along a longitudinal joint to form a sheet;

(e) providing the sheet with a smooth surface at the longitudinal joint;

(f) plating the sheet with a metallic material selected from among the group consisting of chromium, nickel, platinum, or silver;

(g) heat treating the sheet by passing it under tension through a reducing atmosphere at an elevated temperature, and then cooling the sheet to obtain a high hardness level in the core of the first region; and (h) perforating the sheet to define at least one blade blank having a first region formed of the laminate and a second region formed of the strip.

The step of forming the blade blanks from the heat treated sheet may be performed using either an EDM process, a conventional blade blanking process, or other metal cutting process. Alternatively, the blade blanking or EDM process may be performed on the composite sheet prior to heat treatment to harden the core material.

The method further comprises forming each blank into a surgical blade by securing a heating element to the first region and sharpening the blade blank to provide a sharp cutting edge on the first region. This sharpening step may be performed either before or after the heating element is applied. The method therefore comprises the additional steps of:

(i) coating one side of the plated blank with a first layer of a high expansion dielectric material having a thermal expansion coefficient in the range of the thermal expansion coefficient of the pair of outer layers of the first region and the material of the second region;

(j) depositing a thin layer of a first resistive conductor material in a first pattern on the first layer of dielectric material;

(k) depositing a thin layer of a second resistive conductor material in a second pattern on the first dielectric layer superimposed over the second region, the second pattern overlapping the first pattern of first dielectric material so that the first and second resistive conductors are in electrical contact;

(l) depositing a second layer of dielectric material over the first and second patterns of resistive conductive material except for a portion of the second pattern that is left exposed to accommodate completing an electrical contact between the resistive conductor materials and the electrical terminal of the handle; and (m) sharpening the blade to form a sharpened blade having a cutting edge.

The method of the present invention further includes those process steps described above with respect to Examples I and II, for example, coating the blade with coating 19 of abherent material.

It is to be understood that the various aspects of the present invention also are applicable to medical devices other than hemostatic surgical blades, and that the various dimensions of the heating element components and the support member may be adjusted for the specific application. One skilled in the art will appreciate that the present invention can be practiced by other than the described embodiments, which are presented for purposes of illustration and not of limitation and that the present invention is limited only by the claims that follow.

What is claimed is:

1. A blade for use in a surgical instrument for hemostatically cutting tissue to reduce bleeding, the instrument including a handle having an electrical terminal, the blade comprising:
   a first region of a laminate material having a cutting edge and two lateral sides, the laminate comprising a core of a high strength hardenable material and a pair of outer layers of a material having a high thermal conductivity, each of the pair of outer layers disposed on opposite sides of the core and in thermal communication therewith;
   a second region comprising a low thermal conductivity metallic material, the second region metallurgically joined to the first region at a longitudinal joint, the longitudinal joint being mechanically finished to provide a smooth surface, the second region having a portion adapted to engage the handle;
   a heating element for heating the first region to a temperature in the range from about 100° C. to about 500° C., the heating element secured to first region in thermal communication therewith and electrically isolated therefrom; and
   an electrical lead for connecting the heating element to the electrical terminal, the electrical lead disposed on the first and second regions and extending continuously across the longitudinal joint.

2. The apparatus of claim 1 wherein the heating element is secured to one of the lateral sides of the first region.

3. The apparatus of claim 1 wherein the heating element further comprises:
   a first thin layer of dielectric material having high thermal conductivity disposed on the first region; and
   a resistive conductor material disposed on first dielectric material, the resistive conductor material having a first resistivity and a resistance that vary as a function of temperature.

4. The apparatus of claim 3 wherein the electrical lead further comprises:
   a second thin layer of dielectric material disposed on the second region; and
   a conductor material having a second resistivity equal to or less than the first resistivity, the conductor material disposed on the second thin layer of dielectric and in electrical contact with the resistive conductor material.

5. The apparatus of claim 4 wherein the heating element further comprises a plurality of segments, each of the segments including a pattern of the resistive conductor material and an electrical lead of the conductor material, so that each of the segments is individually temperature controlled.

6. The apparatus of claim 5 further comprising a third dielectric material disposed on all of the resistive conductor material and the conductor material except for a portion to be electrically connected to the electrical terminal.

7. The apparatus of claim 6 further comprising a layer of abherent material disposed on those portions of the first region, heating element and electrical lead that contact tissue during use.

8. The apparatus of claim 7 wherein the abherent material retains non-stick properties at temperatures in the range from about 100° C. to about 400° C..

9. The apparatus of claim 4 wherein the resistive conductor material and the conductor material comprise the same material.

10. The apparatus of claim 3 wherein the resistive conductor material comprises a glass-based material having an expansion coefficient not less than 12 microinches/inch/°C. and a temperature coefficient of resistance of at least 0.0005 per °C. in the temperature range from about 20° C. to about 400° C..

11. The apparatus of claim 10 wherein the glass-based material is selected from among the group consisting of oxides of silicon, iron, sodium, potassium, calcium, chromium, aluminum, lithium, lead, zinc or combinations thereof.

12. The apparatus of claim 3 wherein the resistive conductor material further comprises a polymer-based material having an expansion coefficient not less than 12 microinches/inch/°C. and a temperature coefficient of resistance of at least 0.0005 per °C. at temperatures in the range from about 20° C. to about 400° C..

13. The apparatus of claim 4 wherein the first and second dielectric materials further comprise a material selected from among the group consisting of diamond or diamond-like forms of carbon, and oxides of silicon, iron, sodium, potassium, calcium, chromium, aluminum, lithium, lead, zinc or combinations thereof.

14. The apparatus of claim 1 wherein the low thermal conductivity metallic material is selected from among the group consisting of the family of austenitic stainless steels.

15. The apparatus of claim 1 wherein the high strength hardenable material is selected from among the group consisting of the family of martensitic stainless steels.

16. The apparatus of claim 1 wherein the high thermal conductivity material comprises aluminum oxide dispersion-strengthened copper having an aluminum oxide content ranging from about 0.1 to about 0.6 percent of aluminum oxide by weight.

17. The apparatus of claim 1 wherein the low thermal conductivity material has a thermal conductivity of not greater than 0.2 cal/sec/cm/°C.

18. The apparatus of claim 1 further comprising a thin film of oxidation resistant material deposited on the cutting edge.

19. A blade for a hemostatic surgical instrument comprising:
   a first region including a portion defining a cutting edge, the first region of a laminate comprising a core of a high strength hardenable material having lateral faces, and first and second outer layers of a high thermal conductivity material, each one of the first and second outer layers joined to one of the material faces of the core;
   a second region of a low thermal conductivity material welded to the first region at a longitudinal joint, the longitudinal joint mechanically finished to provide a smooth surface, the blade being heat treated while in blank form by passing it through a reducing atmosphere at an elevated temperature and then being cooled to obtain a high hardness level in the core of the first region;
   a first layer of a high expansion dielectric material coated on the first and second regions, the first layer having a thermal expansion coefficient in the range of the thermal expansion coefficient of one of the pair of outer layers of the first region and the low thermal conductivity material of the second region;
   a resistive conductor material deposited in a first pattern of the first layer of dielectric material so that the first pattern is superimposed over the first region, the resistive conductor material having a specific sheet resistance in the range of from about 10 to about 50 milliohms per square mm at 20° C.;
   a conductor material deposited in a second pattern on the first dielectric layer superimposed over the second region, the second pattern overlapping the first pattern of first dielectric material so that the resistive conductor material and the conductor material are in electrical contact; and
   a second layer of dielectric material deposited over all of the first pattern and the second pattern except for a portion adapted for completing an electrical contact between the conductor material and the hemostatic surgical instrument.

20. The blade as defined in claim 19 further comprising a layer of material deposited on the blade while still in blank form and after heat treatment, the layer of material selected from among the group consisting of chromium, nickel, platinum or gold.

21. The blade as defined in claim 19 wherein the second region is electron beam welded to the first region.

22. The blade as defined in claim 19 wherein the blade, while in blank form, is heated during heat treatment to a temperature of about 1,000° C. or greater.

23. The blade as defined in claim 19 wherein the first layer of a high expansion dielectric material is coated on the first and second regions by thick-film printing.

24. The blade as defined in claim 19 wherein the first layer of a high expansion dielectric material is coated on the first and second regions by vapor deposition of diamond or diamond-like carbon.

25. The blade as defined in claim 19 wherein the resistive conductor material is deposited by thick-film printing, the resistive conductor material selected from among the group consisting of a metal-filled glass containing silver or a high-expansion metal-filled, polymer-based conducting material.

26. The blade as defined in claim 19 wherein the resistive conductor material is deposited by vapor or thermal deposition of a metal-filled glass.

27. The blade as defined in claim 19 wherein the conductor material is deposited by thick-film printing and comprises a high-expansion metal-filled, polymer-based conducting material.

28. The blade as defined in claim 19 further comprising:
   a layer of an abherent material coating those portions of ht first and second regions that contact tissue during use of the blade, the layer of abherent material coated on the blade by dip coating the blade in the abherent material and air drying the blade at about 120° C. for from about 10 to about 30 minutes, followed by heating the blade at about 350° C. for from about 10 to about 20 minutes.

29. The blade as defined in claim 19 further comprising:
   a thin layer of oxidation resistant material deposited on the cutting edge.

* * * * *